(12) United States Patent
Sapian

(10) Patent No.: US 6,939,135 B2
(45) Date of Patent: Sep. 6, 2005

(54) GROWTH FACTOR RELEASING BIOFUNCTIONAL DENTAL IMPLANT

(76) Inventor: Schubert L. Sapian, 3412 Kingfisher La., Denton, TX (US) 76201

(*) Notice: Subject to any disclaimer, the term of this patent is extended or adjusted under 35 U.S.C. 154(b) by 304 days.

(21) Appl. No.: 10/159,644

(22) Filed: Jun. 3, 2002

(65) Prior Publication Data
US 2003/0224328 A1 Dec. 4, 2003

(51) Int. Cl.[7] ................................................. A61C 8/00
(52) U.S. Cl. .............................................. 433/174
(58) Field of Search ................................ 433/172, 173, 433/174

(56) References Cited

U.S. PATENT DOCUMENTS

| | | | | |
|---|---|---|---|---|
| 4,324,550 A | * | 4/1982 | Reuther et al. | 433/174 |
| 4,431,416 A | * | 2/1984 | Niznick | 433/174 |
| 4,657,510 A | * | 4/1987 | Gittleman | 433/173 |
| 4,746,293 A | * | 5/1988 | Lundgren et al. | 433/173 |
| 4,907,969 A | * | 3/1990 | Ward | 433/173 |
| 4,957,437 A | * | 9/1990 | Shimura et al. | 433/169 |
| 5,098,294 A | * | 3/1992 | Lee et al. | 433/169 |
| 5,178,539 A | * | 1/1993 | Peltier et al. | 433/173 |
| 5,246,369 A | * | 9/1993 | Poulmaire | 433/173 |
| 5,362,234 A | * | 11/1994 | Salazar et al. | 433/169 |
| 5,417,569 A | * | 5/1995 | Perisse | 433/173 |
| 5,658,146 A | * | 8/1997 | Kisielewski et al. | 433/172 |
| 5,752,830 A | * | 5/1998 | Suarez | 433/173 |

* cited by examiner

Primary Examiner—Todd E. Manahan
(74) Attorney, Agent, or Firm—Morland C. Fischer (57) ABSTRACT

A biofunctional dental implant system for affixing a crown to an implant socket that is made in the bone structure within the mouth of a dental patient. A root portion is initially anchored within the implant socket made in the patient's bone structure. According to a first embodiment of this invention, the crown is secured to the root portion by a flexible abutment post. According to a second embodiment, the crown is secured to the root portion by a hollow abutment tube. The dental implant system of this invention is capable of increasing bone/implant stabilization and providing a supply path through which to evenly distribute human growth factor to the bone structure surrounding the root portion. The system also enables the crown to have a selectively controllable mobility relative to the root portion that is anchored within the implant socket so as to advantageously function like a natural tooth.

10 Claims, 8 Drawing Sheets

GROWTH FACTOR RELEASING BIOFUNCTIONAL DENTAL IMPLANT

BACKGROUND OF THE INVENTION

1. Field of the Invention

This invention relates to a biofunctional dental implant including a dental crown and an implant bone locking mechanism by which to anchor the crown within an installation socket that is made in the patient's bone structure to facilitate a reliable bone implant, increase bone/implant stabilization and provide a supply path through which human growth factor can be evenly distributed to the bone structure surrounding the locking mechanism. The crown and the implant bone locking mechanism are coupled to one another to permit the crown to have mobility relative to the locking mechanism and thereby function like a natural tooth.

2. Background Art

Natural teeth in the human mouth are supported in bone by periodontal fibers that function as shock absorbers when a compressive force is applied, such as during chewing. Through disease, accidental injury, anatomical abnormalities, age, and the like, a natural tooth may be removed or missing such that a dental appliance or prosthetic device (e.g. a crown) is implanted in the patient's bone structure to improve the patient's physical appearance and/or quality of mastication. However, conventional implants are often too rigid to function like natural teeth. Problems such as crown breakage, screw loosening and screw breakage are inherent problems with a rigid crown implant. Failure is also known to occur when an implant is used in a bridge abutment with a natural tooth or when improper occlusion is created by the implant crown.

More particularly, screws associated with conventional crowns sometimes break because of over tightening and due to tension and lateral stress to which the crown is subjected during use. Moreover, a single crown can rotate in response to high lateral and torquing forces encountered while chewing, whereby to rotate and loosen screws. As dental professionals will understand, it is difficult and time consuming to retrieve and/or repair such broken screws. In addition, special purpose torque drivers are required to install the screws. Once the root portion of the implant is installed, it may take several months to achieve suitable bone integration of the root portion with the surrounding bone structure thereby resulting in increased loading time before the crown can be reliably anchored. What is still more, many crowns are not adapted to move under loading conditions and, consequently, they cannot easily absorb and distribute shock and other physical forces that are generated during chewing. Such crowns may be susceptible to damage or reduced life and may be unable to provide the function of a natural tooth and the quality of mastication associated therewith.

Accordingly, it would be desirable to overcome the problems associated with conventional crowns by avoiding screws which can break or loosen and the special purpose tools that are needed to install such screws. It would also be desirable to decrease integration time by increasing stabilization between the root portion of the implant and the bone structure of the patient and by promoting tissue growth around the root portion to help anchor the root portion in place and thereby avoid damage to the surrounding bone structure. It would be further desirable that the crown be capable of moving during chewing so as to emulate a natural tooth. Therefore, patient comfort will be enhanced, the life of the crown will be increased, and the need to make repairs (along with the follow-up visits and corresponding cost) can be reduced.

In my U.S. Pat. No. 5,890,902 issued Apr. 6, 1999, a reliable solution is provided to overcoming the problems described above. By virtue of the embodiments disclosed below, additional solutions are provided that are characterized by few component parts, relative ease in manufacture and installation, and a correspondingly reduced manufacturing cost.

SUMMARY OF THE INVENTION

An implant bone locking mechanism is disclosed having a root portion located below a dental patient's gum line and anchored within an implant socket that is made in the patient's bone structure. A dental crown is coupled to the root portion so as to have mobility relative thereto and emulate the function of a natural tooth. The root portion includes a generally cylindrical implant casing having an outwardly flared implant cradle at one end upon which the crown portion is slidably supported. The implant cradle includes an installation opening which communicates with a screw threaded central passage that extends longitudinally through the implant casing. The installation opening is sized to receive therein a suitable tool by which to impart a vertical and/or rotational force to the implant casing for advancing the root portion into the implant socket made in the patient's bone structure.

According to a first embodiment of this invention, a plurality of growth factor ports are formed through the implant casing so that a supply of human growth factor can be evenly distributed to the patient's bone structure. The crown portion is connected to the root portion by means of a flexible abutment post having screw threaded coronal and apical ends. The screw threaded apical end of the abutment post is rotated into mating engagement with the screw threaded central passage that extends longitudinally through the implant casing. The screw threaded coronal end of the abutment post projects upwardly from the implant casing for receipt within a cavity that is formed in the crown portion. A compressible washer is located within the cavity of the crown portion so as to surround the coronal end of the abutment post. A threaded nut is rotated around the screw threaded coronal end and moved against the washer. The mobility of the crown portion over the implant cradle of the implant casing is selectively controlled by tightening the threaded nut and thereby compressing the compressible washer to secure the crown portion against the implant cradle. The cavity formed in the crown portion is then filled and closed by a composite filler.

According to a second embodiment of this invention, a plurality of growth factor ports are formed through the implant casing so that a supply of human growth factor can be evenly distributed to the patient's bone structure. A corresponding plurality of locking pins are slidable outwardly through respective growth factor ports for biting into the patient's bone structure and thereby anchoring the root portion within the implant socket. The crown portion is connected to the root portion by means of a hollow abutment tube having upper and lower screw threaded cylindrical ends. The lower screw threaded cylindrical end of the abutment tube is rotated into mating engagement with the screw threaded central passage that extends longitudinally through the implant casing. The upper screw threaded cylindrical end of the abutment tube projects upwardly from the implant casing for receipt within a cavity that is formed in the crown portion. A spring-like washer having flexible outstretched arms is located within the cavity of the crown portion so as to surround the upper screw threaded cylindrical end. The flexible arms of the washer are seated upon a compressible base of the crown portion that surrounds the cavity formed therein. A threaded nut is rotated around the screw threaded upper cylindrical end of the abutment tube and moved against the outstretched flexible arms of the washer. The mobility of the crown portion over the implant cradle of the implant casing is selectively controlled by tightening the threaded nut to cause the flexible arms of the spring-like washer to bend against the compressible base for compressing the base to secure the crown portion against the implant cradle. The cavity in the crown portion is then filled and closed with a composite filler.

DETAILED DESCRIPTION

Figure 1:
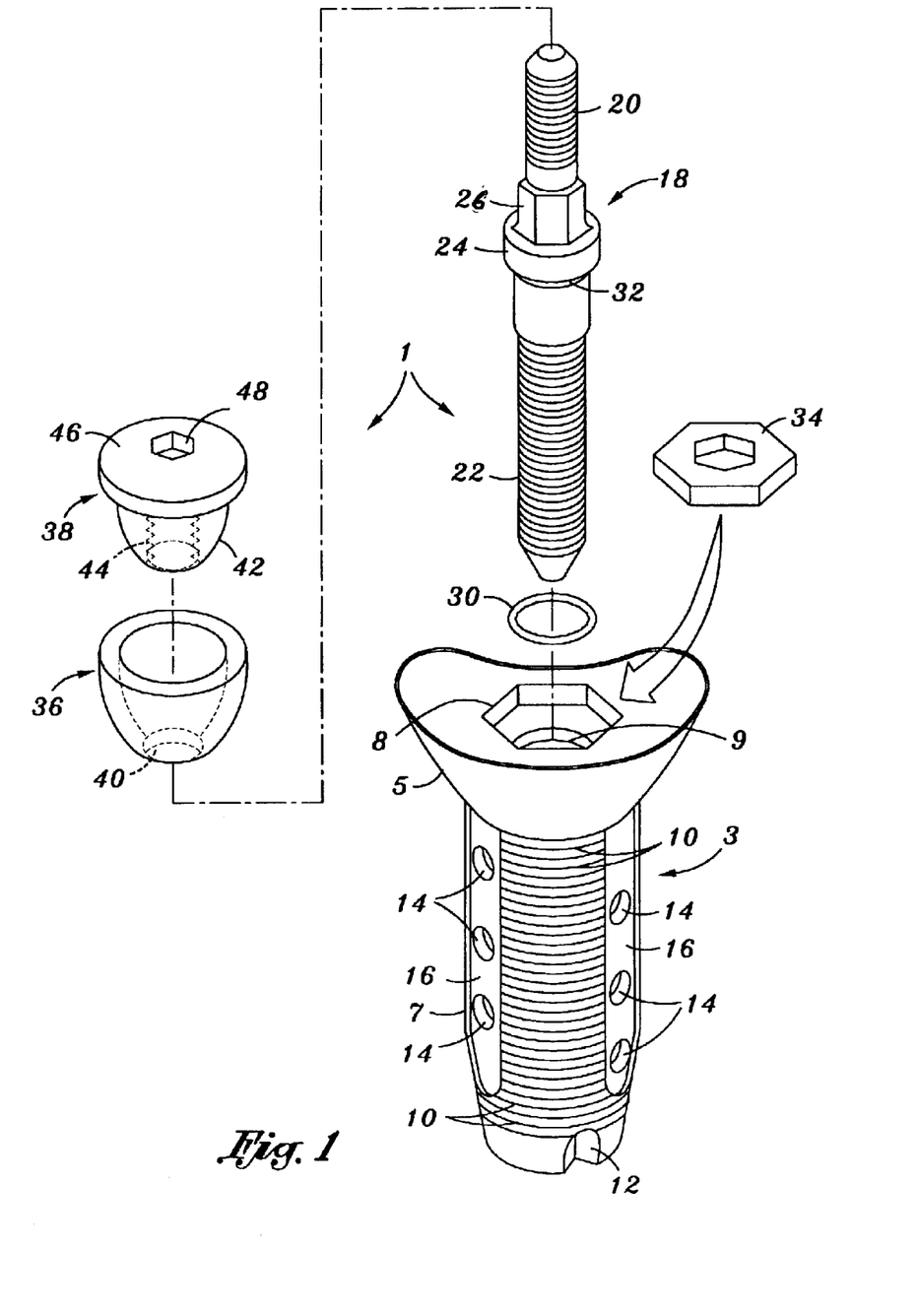
FIG. 1 is an exploded view of an implant bone locking mechanism which forms a first embodiment of this invention.
Figure 2:
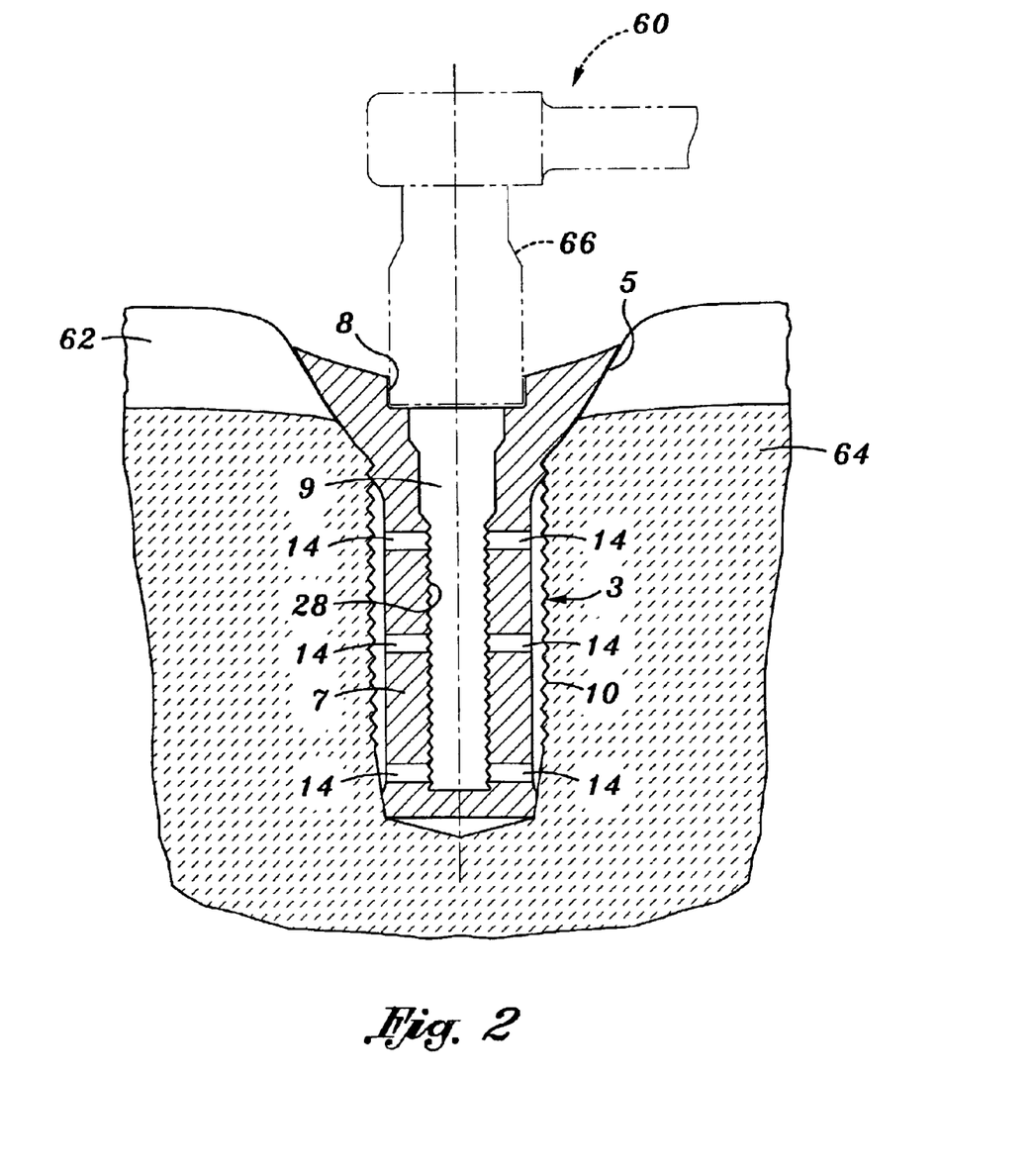
FIG. 2 shows a root portion of the implant bone locking mechanism of FIG. 1 being installed within an implant socket made in the patient's bone structure.

Referring to FIG. 1 of the drawings, there is shown an exploded view of an implant bone locking mechanism 1 which forms a first embodiment of this invention. The implant bone locking mechanism 1 includes a root portion 3 that is preferably manufactured from a biocompatible metallic (e.g. titanium or titanium alloy) or ceramic material that is adapted to be implanted in a socket formed in the bone structure of a dental patient in a manner that will be described in greater detail when referring to FIG. 2. The root portion 3 includes a relatively wide, outwardly flared implant cradle 5 and a relatively narrow, generally cylindrical implant casing 7 which depends downwardly therefrom. As is best shown in FIG. 2, the implant casing 7 of root portion 3 is implanted (by means of a suitable tool 60) within an implant socket that is made in the patient's bone structure so that the implant cradle 5 can support a crown portion (designated 50 in FIG. 5) above the gum line.

Figure 5:
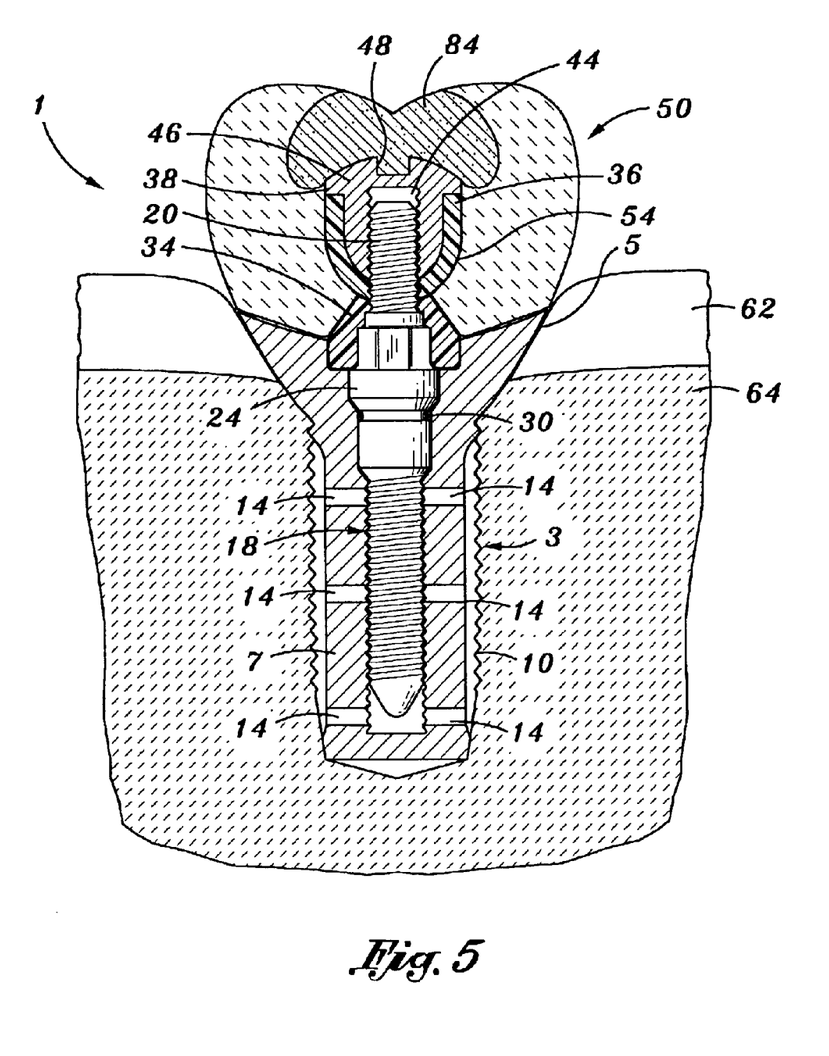
FIG. 5 shows a dental crown of the first embodiment coupled to the abutment post and thereby connected to the root portion so as to have mobility relative thereto.

As shown in FIG. 1, the outwardly flared implant cradle 5 of root portion 3 has a concave shape to receive thereagainst the crown portion 50 (best shown in FIG. 5). However, depending upon the configuration of the crown portion, the implant cradle 5 may also have a convex shape to prevent a rotation of the crown portion. It may be desirable to cover the top of implant cradle 5 with a low friction coating (e.g. such as that known as Teflon) so as to minimize friction at the interface of the crown portion with the implant cradle. What is more, a resilient, biocompatible material may be used to cover the aforementioned low friction coating over implant cradle 5 so as to provide the crown portion with a cushion surface on which to be seated. The side walls of implant cradle 5 are preferably smooth and polished so as to facilitate a close fit within an implant socket formed in the patient's bone structure (best shown in FIG. 2) as well as provide an area to which the patient's gum tissue can bond and/or allow epithelial attachment of gum tissue.

A hexagonal installation opening 8 formed through the top of the implant cradle 5 of root portion 3 communicates with an elongated central passage 9 that extends longitudinally through the interior of implant casing 7 to receive a soon to be described abutment post 18 therewithin. The precise shape of installation opening 8 will depend upon the corresponding shape of the abutment post 18.

The generally cylindrical implant casing 7 of root portion 3 includes a series of sharp threads 10 running circumpherencially therearound and one or more tapping notches 12 formed at the bottom thereof. The sharp threads 10 and tapping notches 12 of implant casing 7 help the root portion 3 of locking mechanism 1 to cut through the patient's bone structure during installation and then resist being pulled out of the implant socket. Vertical rows of radially extending human growth factor ports 14 are spaced around the implant casing 7. Each row of ports 14 terminates at a longitudinally extending channel 16 formed in the implant casing 7. The radially extending ports 14 communicate with the longitudinally extending central passage 9 through the interior of implant casing 7 so that human growth factor can be expulsed and evenly dispersed within the implant socket, the advantages of which will be described in greater detail when referring to FIG. 2.

The abutment post 18 of the implant bone locking mechanism 1 is manufactured from a flexible material, such as a non-metallic composite (e.g. comprising woven carbon fibers) or a metal (e.g. comprising spring steel). The flexible abutment post 18 includes an externally threaded coronal end 20 and an externally threaded apical end 22. Each of the coronal end 20 and the apical end 22 of abutment post 18 terminates at a tapered tip. Located at the approximate midsection of abutment post 18 between the opposite coronal and apical ends 20 and 22 is a wide, disk-like body 24. A (e.g. hexagonal) working surface 26 is located between the body 24 and the coronal end 20 of abutment post 18 to which a torquing force is applied by means of a suitable tool (e.g. the socket wrench designated 80 in FIG. 4) in order to cause the threaded apical end 22 of abutment post 18 to be rotated into the installation opening 8 in implant cradle 5 and downwardly through the longitudinally extending central passage 9 in the implant casing 7 of root portion 3.

In this regard, and as is best shown in FIG. 2, a series of threads 28 runs along the central passage 9 at the interior of the implant casing 7 by which the threaded apical end 22 of abutment post 18 is moved into mating engagement with the root portion 3. To facilitate the aforementioned mating relationship with the internal threads 28 of the implant casing 7 via installation opening 8 and central passage 9, the externally threaded apical end 22 of abutment post 18 may be covered with a low friction (e.g. Teflon) coating.

After the threaded apical end 22 of abutment post 18 has been moved past the installation opening 8 of implant cradle 5 and advanced downwardly through the central passage 9 that runs longitudinally through the implant casing 7 of the root portion 3, the crown portion (designated 50 in FIG. 5) can be mated to the threaded coronal portion 20 of abutment post 18. To this end, an elastomeric sealing ring 30 is seated within a correspondingly shaped groove 32 that surrounds the abutment post 18 immediately below the body 24 thereof so as to prevent an exchange of fluids and block contaminants from invading the installation opening 8 within which the threaded apical end 22 of abutment post 18 is received. Moreover, a suitable (e.g. polyvinyl) sealant is injected into the installation opening 8 of implant cradle 5 by which to form a solid (e.g. hexagonal) washer 34 to lock the body 24 of abutment post 18 to the implant cradle 5 at the top of root portion 3.

The implant bone locking mechanism 1 also includes the combination of a compressible washer 36 and an adjustable nut 38. The compressible washer 36 is manufactured from a biocompatible elastomer (e.g. silicone flouro-polyvinyl or rubber). The washer 36 has a cup shape with an opening 40 formed through the bottom thereof. In the installed implant configuration of FIG. 5, the cup shaped flexible washer 36 surrounds the abutment post 18 such that the threaded coronal end 20 of the abutment post 18 is received through opening 40.

Seated within the cup shaped compressible washer 36 is the adjustable nut 38. The nut 38 is manufactured from a relatively hard metal (e.g. titanium or a titanium alloy) or plastic (e.g. polyurethane) material. The bottom 42 of the adjustable nut 38 is bowl shaped and sized to form a snug fit within the cup of compressible washer 36 (best shown in FIG. 5). Adjustable nut 38 has a threaded channel 44 running longitudinally through the bottom thereof. In the installed implant configuration of FIG. 5, the channel 44 running through the bottom of nut 38 and the opening 40 formed in the bottom of washer 36 are axially aligned with one another so as to receive the threaded coronal end 20 of abutment post 18. Positioned opposite the bowl shaped bottom 42 and lying across the top of nut 38 is a generally flat, disk shaped cap 46. A (e.g. hexagonal) aperture 48 is formed through the cap 46 to receive a suitably sized tool therewithin. The functions of the compressible washer 36 and the hard, adjustable nut 38 with each other and with the crown portion 50 will be described hereinafter when referring to FIG. 5.

FIG. 2 of the drawings illustrates the steps for installing the root portion 3 of the implant bone locking mechanism 1 of FIG. 1. After a portion of the patient's gum tissue 62 has been removed, a hole is drilled through the underlying bone structure 64 by means of a suitable drilling tool, such as a conventional drill bit (not shown) of the type commonly used in dentistry for the installation of dental implants. Then, a commercially available dental handpiece (e.g. wrench 60) having a torque applicator 66 that is sized to be received within the installation opening 8 at the top of the implant cradle 5 of root portion 3 is rotated so as to apply corresponding rotational and vertical forces by which the implant casing 7 is screwed downwardly into the implant socket created in the patient's bone structure 64. During installation, the sharp external screw threads 10 of implant casing 7 bite into the surrounding bone structure 64 to prevent an inadvertent removal of the root portion 3 therefrom.

Next, a human tissue growth factor, such as bone morphogenic proteins, platelet derived growth factors, insulin derived growth factors, or the like, is injected down the central passage 9 that runs through the interior of implant casing 7 of root portion 3 in communication with the rows of radially extending growth factor ports 14 and the longitudinally extending channels 16. Thus, a supply of human growth factor can be evenly distributed to the surrounding bone structure 64 for the purpose of decreasing the bone-to-implant integration time.

Figure 3:
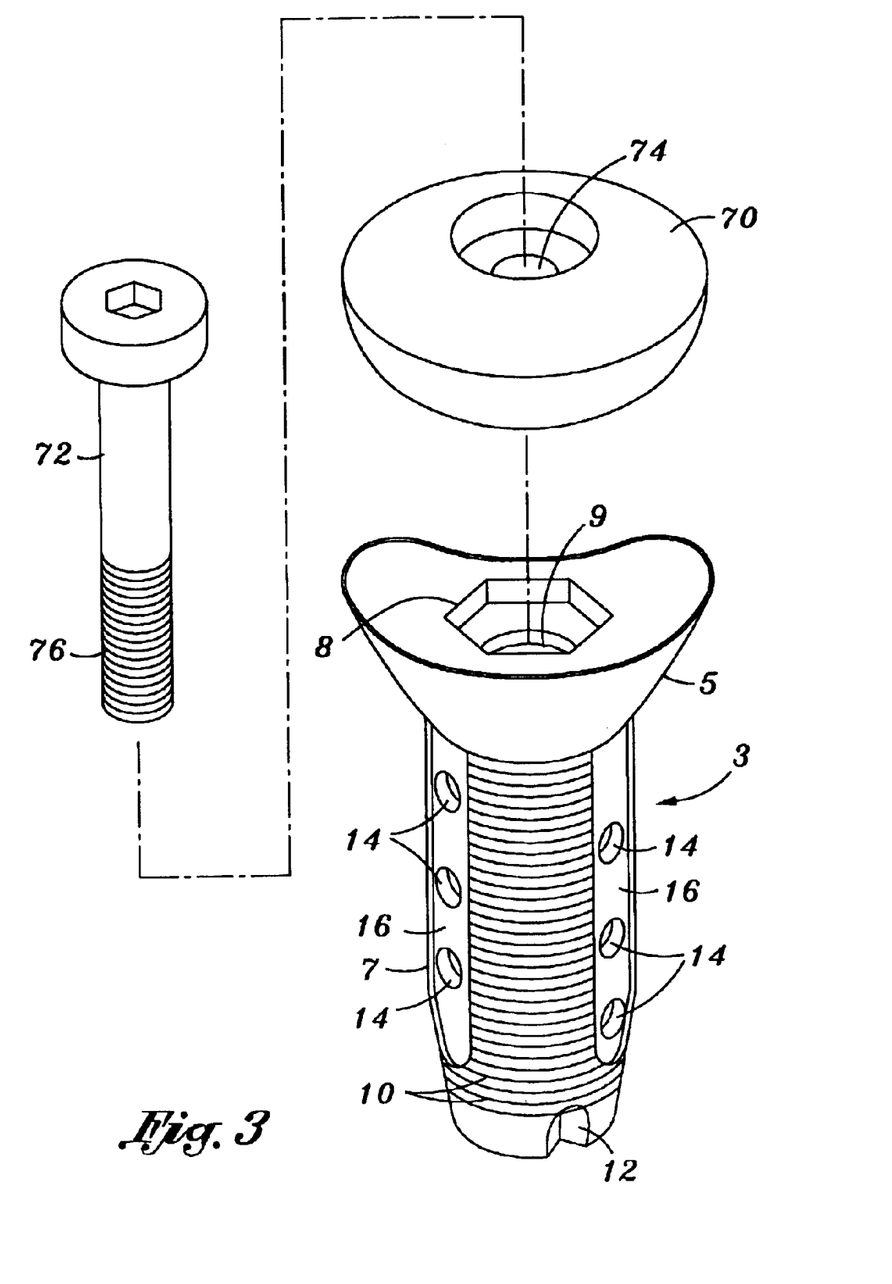
FIG. 3 shows a healing cap to temporarily cover the root portion so as to permit the patient's bone structure to heal following installation of the root portion within the implant socket.

The implant cradle 5 of root portion 3 is now disposed at the top of the implant socket through the patient's bone structure 64 for receipt of the flexible abutment post 18 of locking mechanism 1. However, prior to the installation of the abutment post 18 to root portion 3, it may be desirable to provide the patient with healing time, particularly in situations where the root portion 3 is installed within an implant socket that has been drilled in soft bone. In this case, and referring to FIG. 3 of the drawings, a biocompatible healing cap 70 is temporarily held in place atop the implant cradle 5 of root portion 3 by means of a suitable threaded fastener 72 so as to cover the central passage 9 through implant casing 7. The threaded fastener 72 is rotated downwardly through a hole 74 formed in the top of healing cap 70 for receipt by the longitudinally extending central passage 9 at the interior of implant casing 7. A threaded end 76 of fastener 72 is mated to and retained by the internal threads (designated 28 and best shown in FIG. 2) of central passage 9. The healing cap 70 may be held in place above implant cradle 5 for a sufficient healing time, such as until the occurrence of bone osseo-integration. At this point, the threaded fastener 72 is rotated out of engagement with the implant casing 7 and the healing cap 70 is removed from the implant cradle 5.

Figure 4:
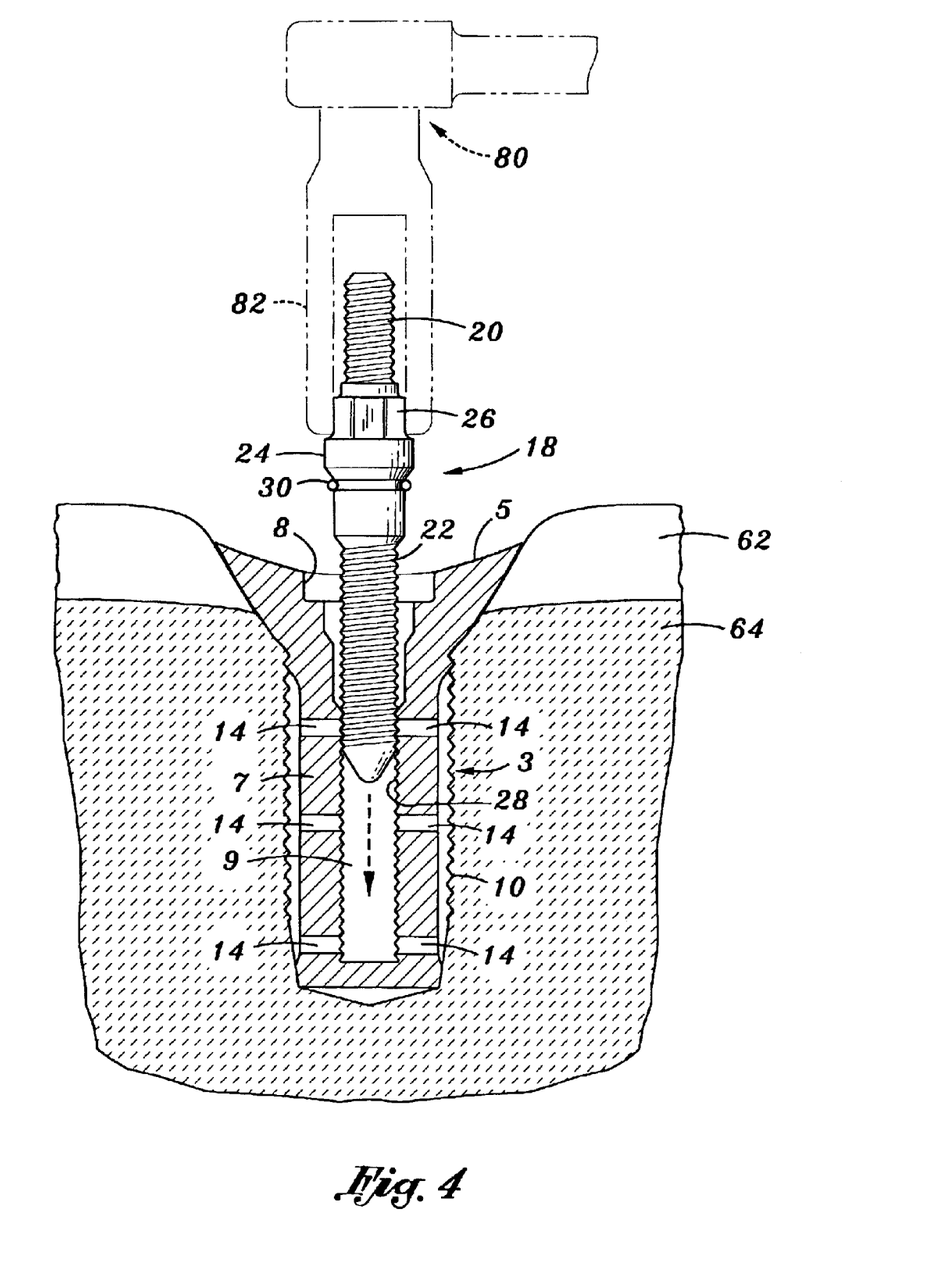
FIG. 4 shows an abutment post of the implant bone locking mechanism of FIG. 1 being mated to the root portion following installation of the root portion within the implant socket.

Turning now to FIG. 4 of the drawings, the flexible abutment post 18 is shown being coupled to the implant casing 7 of root portion 3 that has been installed in the implant socket formed in the patient's bone structure 64. More particularly, either the previously described handpiece (designated 60 in FIG. 2) or a different tool (e.g. a socket wrench 80) is used to surround the hexagonal working surface 26 of abutment post 18. The tool 80 includes a torque applicator 82 that is sized to grip and apply a rotational force to working surface 26 by which to cause the abutment post 18 to rotate. Accordingly, the threaded apical end 22 of abutment post 18 is advanced axially and screwed downwardly into the central passage 9 of implant casing 7 so as to be rotated into mating engagement with the internal threads 28 thereof.

With the flexible abutment post 18 screwed into the central passage 9 of the implant casing 7, the crown portion 50 can be attached to the root portion 3 of the implant bone and locking mechanism 1 in a manner that will now be described while referring to FIG. 5 of the drawings. In the installed implant configuration of FIG. 5, with the root portion 3 embedded within an implant socket in the patient's bone structure 64 and the flexible abutment post 18 secured to implant casing 7, the crown portion 50 is now ready to be attached to the threaded coronal end of abutment post 18 so as to be seated atop the implant cradle 5. The solidified hexagonal lock washer 34 (previously described when referring to FIG. 1) prevents the abutment post 18 from being inadvertently rotated out of engagement with the implant casing 7 of root portion 3.

The crown portion 50 is manufactured from a durable crown material (e.g. gold, ceramic or plastic composite) and includes a longitudinally extending cavity 54 running therethrough. The bottom of cavity 54 receives the cup shaped, compressible washer 36 (also previously described when referring to FIG. 1). The compressible washer 36 and the cavity 54 in which washer 36 is located function as a ball and socket coupling by which to enable the crown portion 50 to slide laterally over the implant cradle 5 during chewing to emulate a natural tooth. The flexible nature of the abutment post 18 facilitates this lateral mobility of the crown portion 50 relative to the fixed root portion 3 of implant bone locking mechanism 1.

The relatively hard nut 38 is then seated inside the cup shaped compressible washer 36. As was described when referring to FIG. 1, in the installed implant configuration, the threaded coronal end 20 of abutment post 18 is received through an opening 40 and a threaded channel 44 that are axially aligned with one another in the washer 36 and the nut 38 by which the aforementioned ball and socket coupling is established to permit the lateral mobility of crown portion 50 over the implant cradle 5 of root portion 3. A tool (e.g. a wrench) is then inserted into the aperture 48 in the cap 46 of nut 38 to rotate the nut 38 at the threaded channel 44 thereof into mating engagement with threaded coronal end 20 of abutment post 18. Inasmuch as the adjustable nut 38 is manufactured from a harder material than the material from which the compressible washer 36 is manufactured, the ability of the crown portion 50 to move is dependent upon the manner in which the adjustable nut 38 is tightened along the coronal end 20 and downwardly against washer 36. That is to say, the more the adjustable nut 38 is rotated along abutment post 18, the more the washer 36 will be compressed so as to reduce the mobility of crown portion 50.

Once the position of the nut 38 is selectively adjusted along the threaded coronal end 20 of abutment post 18 to attach the crown and root portions 50 and 3 together, the aperture 48 in the cap 46 of nut 38 is filled with a sealer. Finally, the top of the cavity 54 running longitudinally through crown portion 50 is filled and closed by a suitable composite filler 84, such as that sold commercially as ESTHET-X. By virtue of the foregoing, the crown portion 50 will closely emulate the movement and appearance of a natural tooth so as to minimize patient discomfort, prolong the life and function of crown portion 50, increase the quality of mastication, and minimize damage to the patient's bone structure 64 to which the root portion 3 of locking mechanism 1 is anchored.

Figure 6:
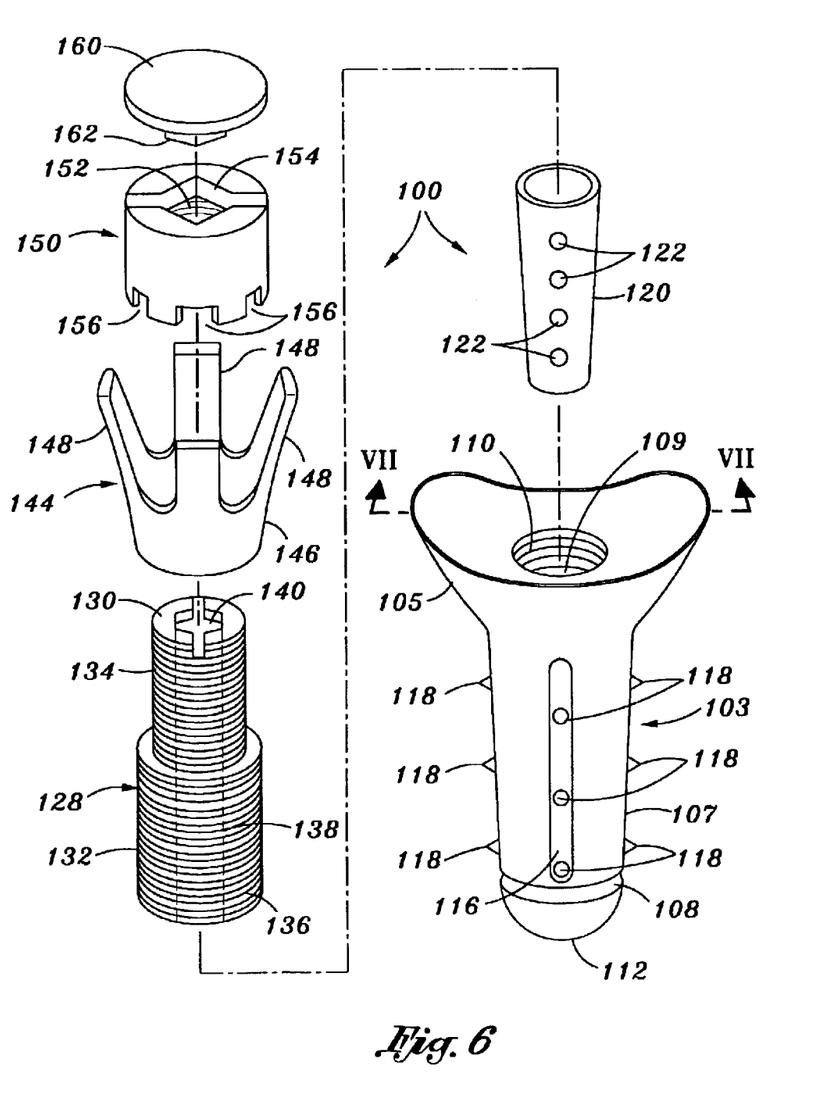
FIG. 6 is an exploded view of an implant bone locking mechanism which forms a second embodiment of this invention.

An exploded view of an implant bone locking mechanism 100 which forms a second embodiment of this invention is now disclosed while referring initially to FIG. 6 of the drawings. Like the locking mechanism 1 of FIGS. 1–5, the implant bone locking mechanism 100 of FIG. 6 includes a metallic (e.g. titanium or titanium alloy) or ceramic root portion 103 that is adapted to be implanted in a socket formed in the bone structure of a dental patient. The root portion 103 includes a relatively wide, outwardly flared implant cradle 105 and a relatively narrow, generally tubular and slightly tapered implant casing 107 depending downwardly therefrom. With the root portion 103 positioned within the implant socket, the implant cradle 105 will be supported above the patient's gum line to receive a crown portion (designated 170 in FIG. 8).

The top of implant cradle 5 may be covered with a low friction (e.g. Teflon) coating to minimize friction at the interface of the crown portion 170 with the implant cradle. What is more, a resilient biocompatible material may be used to cover the low friction coating over implant cradle 105 so as to provide the crown portion with a cushion surface on which to be seated. The side walls of implant cradle 105 are preferably smooth and polished so as to facilitate a close fit within the implant socket formed in the patient's bone structure as well as provide an area to which the patient's gum tissue can bond and/or allow epithelial attachment of gum tissue. In this same regard, a notched ring 108 extends around the bottom of the implant casing 107 to be anchored to the patient's bone structure and prevent an inadvertent removal of root portion 7 from the implant socket following osseo-integration.

Figure 7:
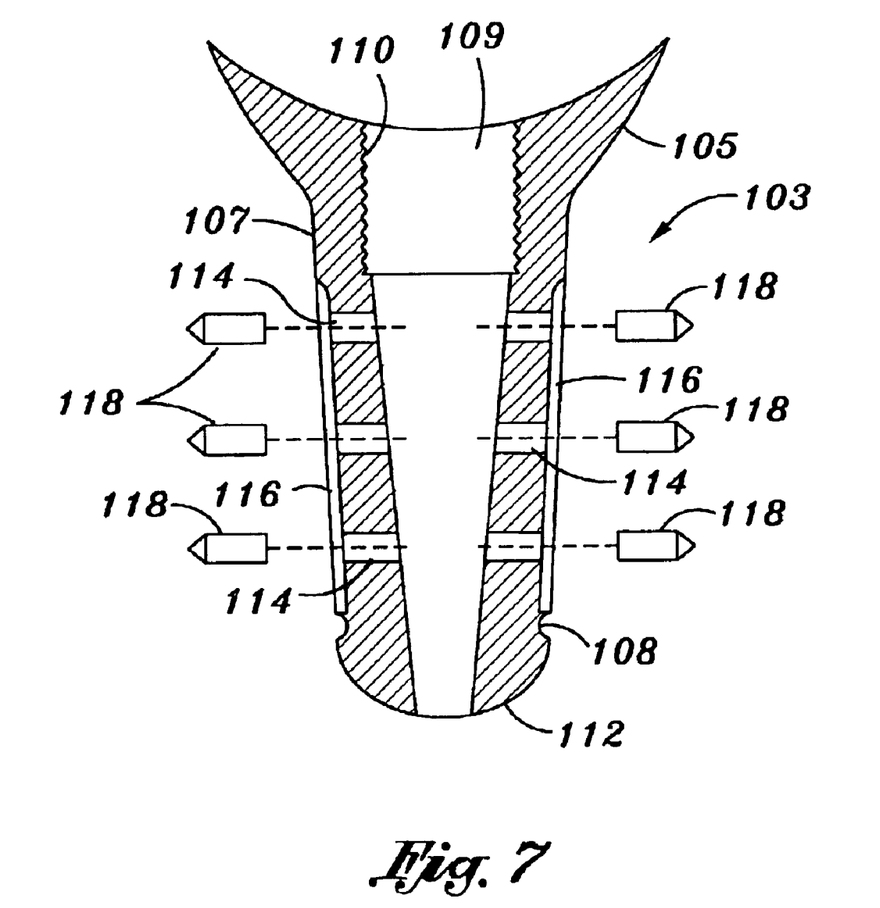
FIG. 7 is a cross-section of an implant casing of the implant bone locking mechanism of FIG. 6 taken along lines 7—7 of FIG. 6.

An elongated central passage 109 extends longitudinally through the implant cradle 105 and the interior of implant casing 107. The bottom of the central passage 109 is tapered while the top of central passage 109 contains a series of screw threads 110 (best shown in FIG. 7). The generally tubular implant casing 107 of root portion 103 includes a rounded bottom end 112 to establish a large surface area for the purpose of absorbing occlusal impaction. Vertical rows of radially extending human growth factor ports 114 (also best shown in FIG. 7) are spaced around the implant casing 107. Each row of ports 114 terminates at an external channel 116 running along the implant casing 107. The radially extending ports 114 communicate with the longitudinally extending central passage 109 through the interior of implant casing 107 so that human growth factor can be expulsed and evenly dispersed within the implant socket within which root portion 3 is received.

The growth factor ports 114 are sized so as to slidably receive respective locking pins 118 having sharp biting tips that are adapted to bore into the patient's bone structure to thereby anchor the root portion 103 of locking mechanism 100. As is best shown in FIG. 6, the growth factor ports 114 through which human growth factor is expulsed and within which the locking pins 118 are slidably received may be formed at staggered locations around the implant casing 107. The locking pins 118 are preferably manufactured from titanium, titanium alloy or hydroxy apatite ceramic. As is also shown in FIG. 6, the locking pins 118 are initially retracted inwardly of the radially extending ports 114 through implant casing 107. However, and as will be explained in greater detail, once the implant casing 107 has been suitably implanted in the patient's bone structure, the locking pins 118 are forced outwardly from their ports 114 and into locking engagement with the surrounding bone structure.

A hollow, sieve-like sleeve 120 is sized and configured to form a snug fit within the central passage 109 of implant casing 107. An impact tool may be used to drive the sleeve 120 through central passage 109 so as to cause the locking pins 118 to move in a radially outward direction from their respective ports 114 to engage the patient's bone structure and thereby anchor the root portion 103. In the alternative, a separate plug (not shown) can be driven downwardly through the central passage 109 of implant casing 107 to cause the locking pins 118 to move radially outward therefrom. A series of seep holes 122 are formed through the sleeve 120. In either case, sleeve 120 blocks a return of the locking pins 118 to the retracted position. In the installed implant configuration of FIG. 8, the sleeve 120 is filled with human growth factor which will drain through seep holes 122 to be delivered to the surrounding bone structure via the radially extending growth factor ports 114 and the longitudinal channels 116 (of FIG. 7) formed in the implant casing 107.

A rigid metal (e.g. titanium or stainless steel) abutment tube 128 is included by which to attach the crown portion (designated 170 in FIG. 8) to the root portion 3 of implant bone locking mechanism 100. Abutment tube 128 includes upper and lower cylindrical bodies 130 and 132. Each of the upper and lower cylindrical bodies 130 and 132 has a set of external screw threads 134 and 136 running continuously therearound. The diameter of the upper cylindrical body 130 of abutment tube 128 is smaller than the diameter of the lower cylindrical body 132. A channel 138 extends longitudinally through the upper and lower cylindrical bodies 130 and 132 of abutment tube 128. A (e.g. hexagonal) installation opening 140 communicates with the channel 138 at the top of the upper body 130.

Figure 8:
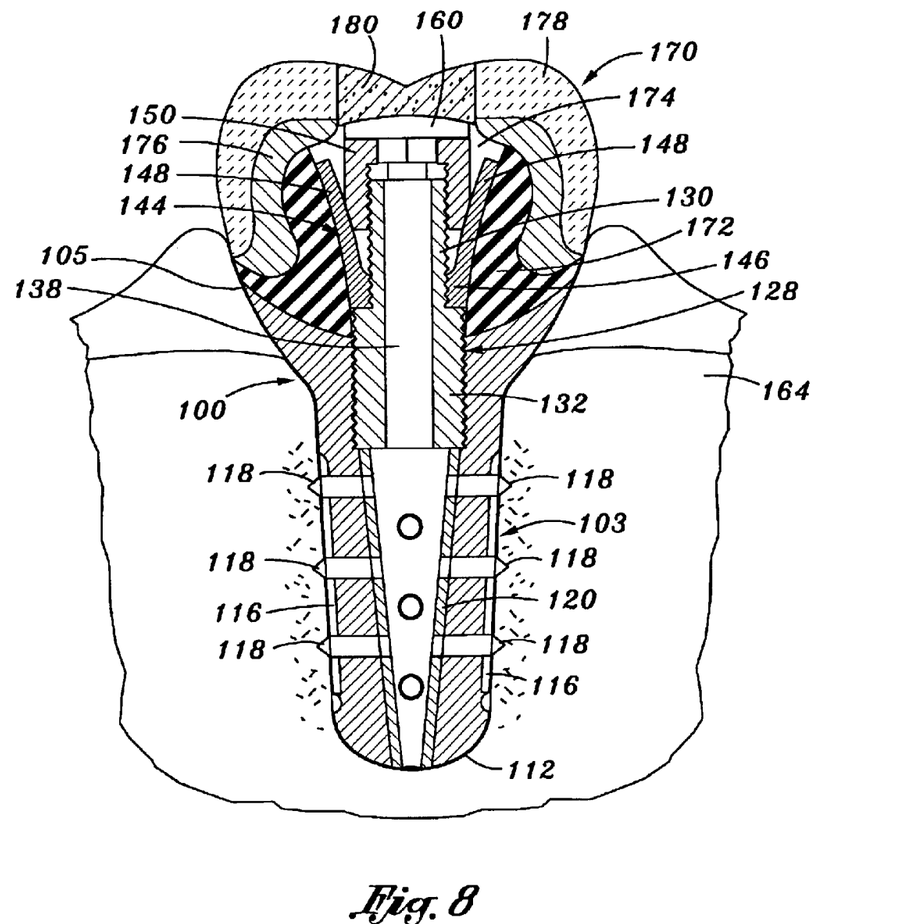
FIG. 8 shows a dental crown of the second embodiment coupled to the abutment tube and thereby connected to the root portion so as to have mobility relative thereto.

To complete the implant configuration of FIG. 8, a suitable tool (not shown) is inserted into the installation opening 140 of abutment tube 128. A rotational force imparted by the tool is transferred to the abutment tube 128, whereby the lower cylindrical body 132 is rotated downwardly and into the central passage 109 of implant casing 107 so as to be received therein above the sieve-like sleeve 120. Accordingly, the external screw threads 136 of the lower cylindrical body 132 are mated to the internal screw threads 110 of the central passage 109.

With the abutment tube 128 attached to the implant casing 107 as just described, the lower cylindrical body 132 pushes downwardly on and retains the sieve-like sleeve 120 within the central passage 109 of implant casing 107 to prevent a displacement thereof. Moreover, the upper cylindrical body 130 of abutment tube 128 now projects outwardly from implant casing 107 so as to lie above the implant cradle 105 of root portion 103 to facilitate the connection of the crown portion in a manner to be described when referring to FIG. 8. The channel 138 extending through the abutment tube 128 creates a supply path for the human growth factor to be delivered to the surrounding bone structure of the patient by way of the seep holes 122 formed in sleeve 120 and the growth factor ports 114 formed in the implant casing 107.

In order to hold the crown portion 170 against the implant cradle 5 of the root portion 3 of implant bone locking mechanism 100, a spring-like washer 144 is provided to exert a downward pushing force against the crown portion. The spring-like washer 144 is manufactured from a flexible metal (e.g. stainless spring steel) and includes a hollow body 146 and a plurality of spring arms 148 spaced around the hollow body 146 and stretching upwardly and outwardly therefrom. The hollow body 146 of washer 144 is sized to surround the upper cylindrical body 130 of abutment tube 128. The outwardly stretched spring arms 148 of washer 144 are flexible and adapted to be pushed downwardly and bent against the crown portion to apply a holding pressure thereagainst.

To control the holding pressure applied against the crown portion by the flexible spring arms 148 of washer 144 in the installed implant configuration of FIG. 8, an adjustable periodontal ligament nut 150 is seated within the spring arms 148. The adjustable nut 150 is manufactured from metal (e.g. stainless steel) and includes a screw threaded channel 152 extending longitudinally therethrough and a (e.g. hexagonal) installation opening 154 that communicates with the threaded channel 152 at the top of nut 150. The threaded channel 152 of nut 150 has a diameter that is sized to surround the threaded upper cylindrical body 130 of abutment tube 128.

With the hollow body 146 of spring-like washer 144 surrounding the upper cylindrical body 130 and seated upon the lower cylindrical body 132 of abutment tube 128, a suitable tool (not shown) is inserted into the installation opening 152 of adjustable nut 150. A rotational force imparted by the tool is transferred to the adjustable nut 150, whereby the nut is coupled to the upper cylindrical body 130 of abutment tube 128.

Accordingly, the screw threaded channel 152 of adjustment nut 150 is mated to the external screw threads 134 of the upper cylindrical body 130 of abutment tube 128. The rotation of the adjustable nut 150 around the upper cylindrical body 130 continues until the nut 150 has been moved downwardly towards and seated within the outwardly stretched spring arms 148 of spring-like washer 144 (best shown in FIG. 8). The adjustment nut 150 can be tightened against the abutment tube 128 so as to selectively control the bending force applied to and the corresponding holding pressure generated by the spring arms 148 of washer 144 for causing the crown portion 170 to be retained at the implant cradle 105 of implant casing 107.

The bottom of the adjustable nut 150 includes a set of flat slots 156 formed therein to accommodate respective outstretched arms 148 of the washer 144. As just described, when the nut 150 is rotated around and tightened downwardly along the upper cylindrical body 130 of abutment tube 128, a bending force will be applied to the arms 148. The axial advancement of the adjustable nut 150 continues until the outstretched arms 148 of washer 144 are received within respective ones of the flat slots 156 (best shown in FIG. 8). With the flexible arms 148 of the spring-like washer 144 captured by the flat slots 156, the adjustable nut 150 will be unable to rotate out of engagement with the upper cylindrical body 130 of abutment tube 128 so as to prevent an inadvertent separation or loosening of the crown portion 170 from the root portion 103.

Once the adjustable nut 150 has been advanced so as to cause the outstretched arms 148 of the spring-like washer 144 to bend and thereby generate a holding pressure for retaining the crown portion 170 against the implant cradle 105 of root portion 103, the installation opening 154 at the top of the nut 150 is closed. The foregoing is accomplished by means of an elastomeric (e.g. rubber) plug 160 having a nub 162 projecting downwardly therefrom and sized for receipt by installation opening 154. In certain cases, it may be desirable to subsequently remove plug 160 from nut 150 to enable a fresh supply of human growth factor to be supplied to the bone structure surrounding the locking mechanism 100 via the supply path including the axially aligned channel 138 through abutment tube 128, the seep holes 122 through sleeve 120, and the growth factor ports 114 through implant casing 107.

Referring now to the installed implant configuration of FIG. 8, the root portion 103 of the implant bone locking mechanism 100 of this embodiment is shown anchored within the implant socket formed in the patient's bone structure 164, and the crown portion 170 is shown connected to the root portion 103. The crown portion 170 is manufactured to include a compressible elastomeric base 172 having a longitudinally extending cavity 174. The bottom of the cavity 174 through base 172 receives therewithin the threaded upper cylindrical body 130 of abutment tube 128 and the spring-like washer 144. The hollow body 146 of washer 144 is seated upon the lower cylindrical body 132 of abutment tube 128 in surrounding engagement with the upper body 130 thereof. Thus, when the adjustable periodontal ligament nut 150 is tightened downwardly along the upper cylindrical body 130 and into contact with the flexible outstretched spring arms 148 of washer 144, the corresponding holding force that is generated as the spring arms 148 are bent is transferred to the compressible base 172 of crown portion 170 by which to retain the crown portion against the implant cradle 105 of root portion 103.

The compressible elastomeric base 172 of crown portion 170 is covered by a metallic coping 176, and the metallic coping 176 is surrounded by a durable crown material 178 (e.g. gold, ceramic or plastic composite). Finally, the top of the longitudinal cavity 174 running through the compressible base 172 is filled and closed with a suitable composite filler 180 (e.g. ESTHET-X) so as to lie above and press downwardly on the rubber plug 160 that is seated atop the adjustable nut 150.

Because of the flexible nature of the spring arms 148 of the washer 144 that generate a holding pressure, the elastomeric base 172 is compressed by which to retain crown portion 170 against the implant cradle 105 of root portion 103. What is more, the crown portion 170 will be capable of sliding laterally over the implant cradle 105. In this regard, the mobility of the crown portion 170 can be selectively controlled depending upon the tightness by which the adjustable nut 150 is rotated around the threaded abutment tube 128 and the bending force applied to the flexible arms 148 of the spring-like washer 144. By virtue of the foregoing, and similar to the crown portion 50 disclosed above when referring above to FIGS. 1–5, the crown portion 170 of FIGS. 6–8 will closely emulate the movement and appearance of a natural tooth so as to minimize patient discomfort, prolong the life and function of the crown portion 170, increase the quality of mastication, and minimize damage to the patient's bone structure 164 to which the root portion 103 of locking mechanism 100 is anchored.

It is to be understood that this invention has application to single crowns, as illustrated in the drawings, or bridge abutments, partial denture attachments, complete dentures, and other uses where an implant must remain immobile, but when it is also desirable to have a dental appliance or prosthetic device that is capable of mobility so as to closely emulate the natural tooth function.

I claim:

1. A biofunctional dental implant system for affixing a crown portion to the bone structure in the mouth of a patient, said dental implant system comprising:
    a root portion to be implanted below the patient's gum line within a socket made in the patient's bone structure;
    means by which to anchor said root portion within the socket made in the padent's bone structure;
    a crown portion;
    a flexible abutment post having a screw threaded coronal end coupled to said crown portion and an opposite screw threaded apical end coupled to said root portion by which to connect said crown portion to said root portion, said flexible abutment post adapted to bend so that said crown portion is movable relative to said root portion anchored within the socket made in the patient's bone structure; and
    a screw threaded nut,
    said crown portion having a cavity within which to receive the screw threaded coronal end of said flexible abutment post, said screw threaded nut located within said cavity and rotated into mating engagement with said screw threaded coronal end, whereby said crown portion is connected to said root portion by way of said flexible abutment post.

2. The dental implant system recited in claim 1, wherein said root portion includes an implant casing to be received within the socket made in the patient's bone structure, said implant casing having a passage running longitudinally therethrough, the screw threaded apical end of said flexible abutment post received within said passage and coupled to said implant casing.

3. The dental implant system recited in claim 2, wherein said means by which to anchor said root portion to the patient's bone structure includes a set of threads at the exterior of said implant casing to bite into the patient's bone structure when the implant casing of said root portion is received within the socket made in the patient's bone structure.

4. The dental implant system recited in claim 2, wherein said implant casing has a set of growth factor parts communicating with said passage running longitudinally therethrough so that a supply of human growth factor can be delivered to the patient's bone structure surrounding said implant casing by way of said passage and said set of growth factor ports.

5. The dental implant system recited in claim 2, wherein said passage running longitudinally through said implant casing includes a series of screw threads extending therearound, said screw threaded apical end of said flexible abutment post being rotated into mating engagement with said screw threaded passage when said apical end is received within said passage, whereby said abutment post is connected to said root portion.

6. The dental implant system recited in claim 5, said flexible abutment post also having a working surface located between the screw threaded coronal and apical ends thereof at which to receive a torquing force for causing said screw threaded apical end to be moved through the screw threaded passage running longitudinally through said implant casing so as to connect said abutment post to said root portion.

7. The denial implant system recited in claim 2, wherein the implant casing of said root portion includes an outwardly flared implant cradle at one end thereof, said crown portion being seated upon and movable relative to said root portion along said implant cradle.

8. The dental implant system recited in claim 7, wherein said implant cradle includes an installation opening aligned axially with the passage running longitudinally through said implant casing, said installation opening being sized to receive therewithin a tool for applying a rotational force to said implant casing and thereby rotating said root portion into receipt by the socket made in the patient's bone structure.

9. The dental implant system recited in claim 1, further comprising a compressible washer positioned within the cavity of said crown portion for surrounding the threaded coronal end of said flexible abutment post and forming a bull and socket with said crown portion, said compressible washer lying between said threaded nut and said crown portion to apply a pushing force for holding said crown portion against said root portion and thereby controlling the movement of said crown portion relative to Said root portion, said threaded nut being rotated around said coronal end and tightened against said compressible washer for compressing said washer and adjusting the pushing force applied by said washer to said crown portion.

10. A biofunctional dental implant system for affixing a crown portion to the bone structure in the mouth of a patient, said dental implant system comprising:
    a root portion to be implanted below the patient's gum line within a socket made in the patient's bone structure, said root portion having a passage running longitudinally therethrough and screw threads extending around said passage;
    means by which to anchor said root portion within the socket made in the patient's bone structure;
    a crown portion having a central opening formed therein and a screw threaded fastener located within said central opening; and
    a flexible abutment post having a screw threaded coronal end mated to said crown portion at the screw threaded fastener located within the central opening thereof and an opposite screw threaded apical end mated to said root portion at the screw threads extending around said passage running longitudinally therethrough whereby said crown portion is connected to said root portion by way of said flexible abutment post, the coronal end of said flexible abutment post adapted to flex so that said crown portion is moveable relative to said root portion.

* * * * *